United States Patent [19]

Schröck

[11] 4,413,501

[45] Nov. 8, 1983

[54] APPARATUS FOR PRESSURE TESTING TUBING

[76] Inventor: Peter Schröck, Im Vogelsang 5, D-6000 Frankfurt am Main, Fed. Rep. of Germany, 90

[21] Appl. No.: 298,046

[22] Filed: Aug. 31, 1981

[30] Foreign Application Priority Data

Mar. 10, 1980 [DE] Fed. Rep. of Germany ....... 3009168

[51] Int. Cl.³ .......................................... G01M 3/04
[52] U.S. Cl. .................................................. 73/49.6
[58] Field of Search ...................... 73/49.1, 49.5, 49.6; 138/94, 31

[56] References Cited

U.S. PATENT DOCUMENTS

| | | | |
|---|---|---|---|
| 1,637,956 | 8/1927 | Moriarty | 73/49.5 |
| 2,665,603 | 1/1954 | Hoffman | 73/49.6 |
| 3,001,802 | 9/1961 | Rebman et al. | 73/49.5 |
| 3,334,515 | 8/1967 | Kost | 73/49.5 |
| 4,192,177 | 3/1980 | Crickard et al. | 73/49.5 |

*Primary Examiner*—James J. Gill
*Assistant Examiner*—Brian Tumm

[57] ABSTRACT

An apparatus for the pressure testing of tubing has two support members which can be urged towards one another, one of which forming a counterbearing for the tubing and the other having a spigot with a conical face which is at least partially insertable in one end of the tube under test to seal it. The support member with the spigot is connected to an actuating spindle which is coaxial with the axis of the spigot and between the actuating spindle and the support member there is a pressure drive including a cylinder and a piston which is connected in tandem with the actuating spindle to bring the spigot into engagement with the tube. The spigot has a duct through which a test medium can be introduced into the tubing.

10 Claims, 7 Drawing Figures

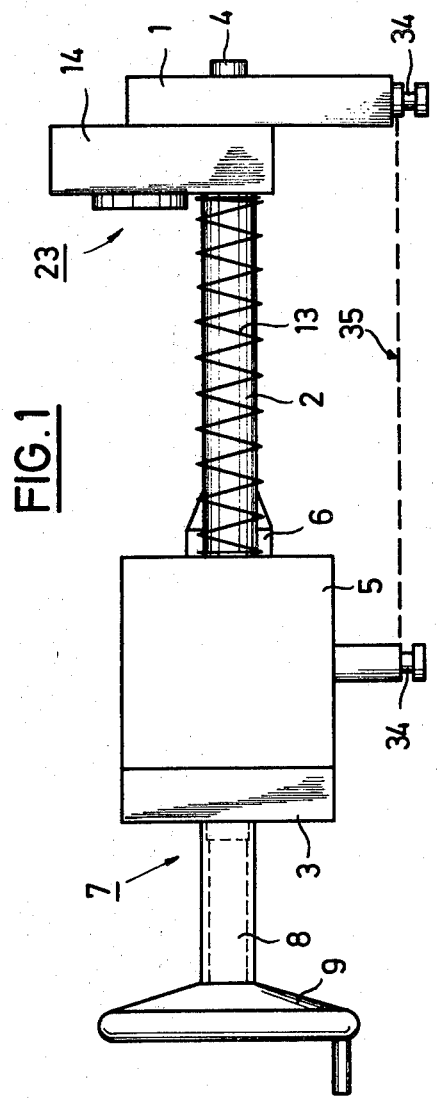
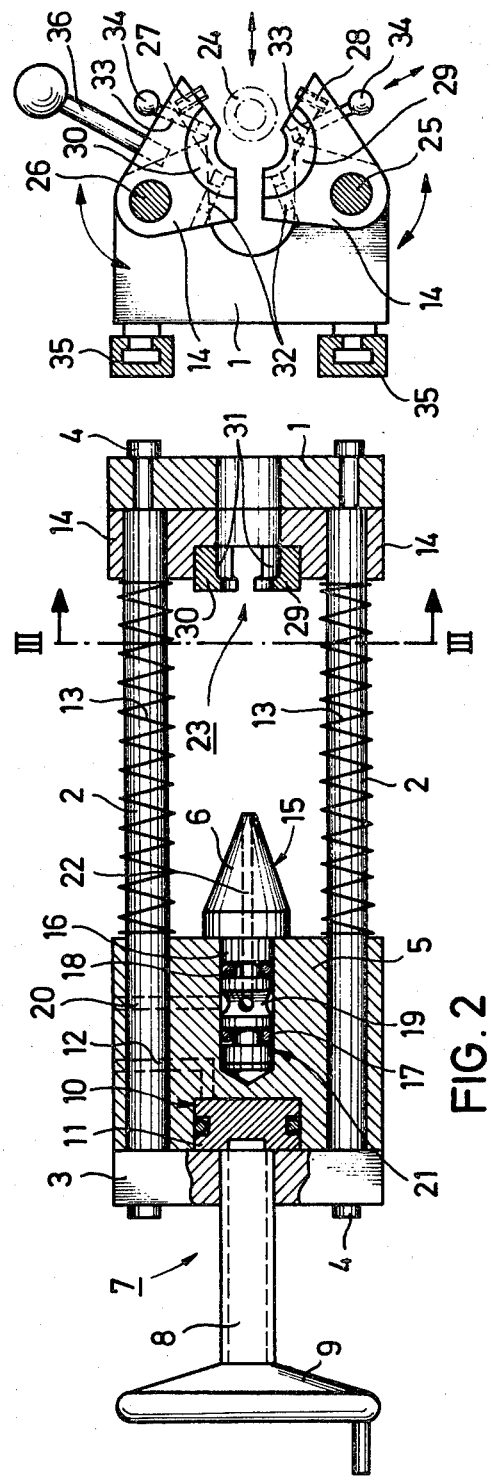

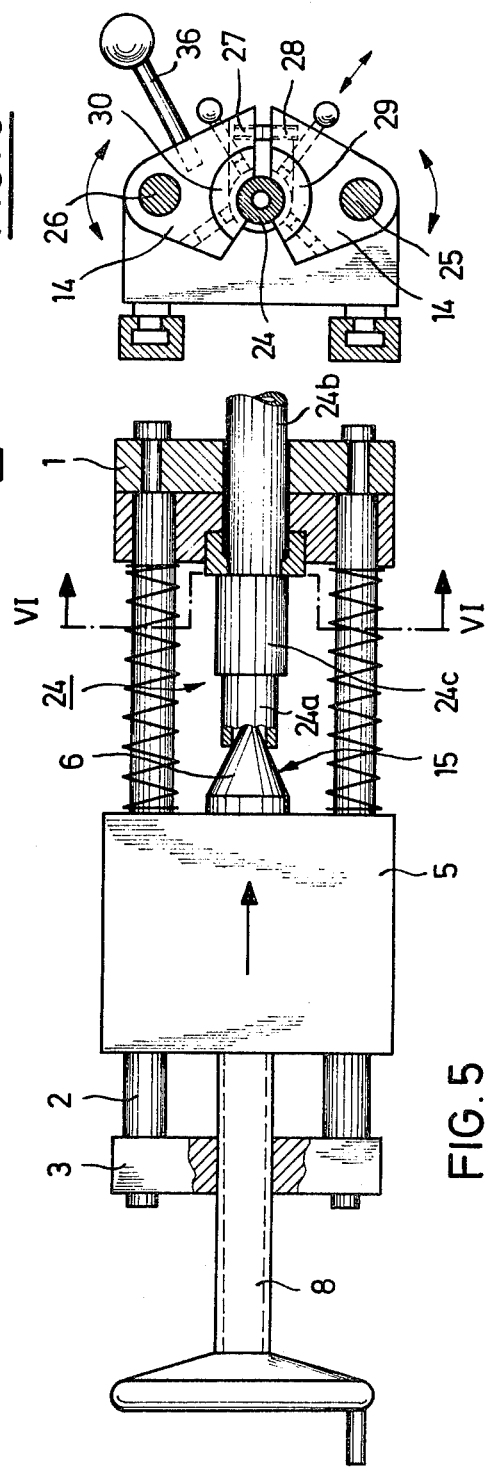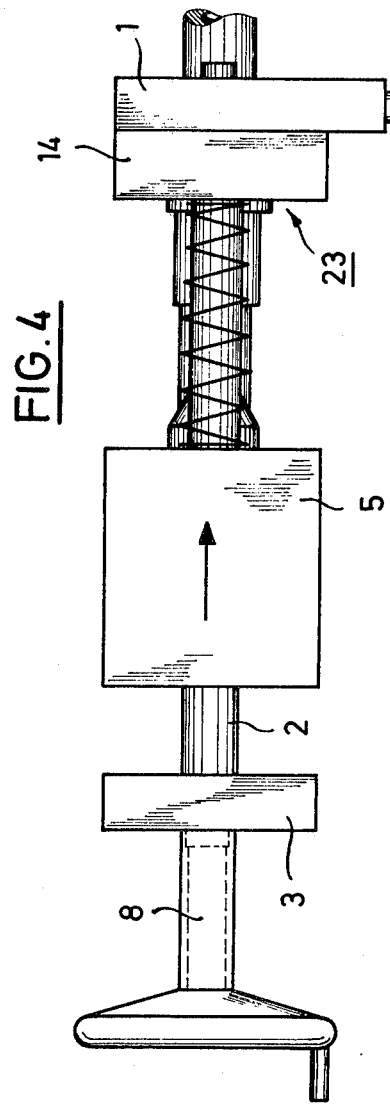

APPARATUS FOR PRESSURE TESTING TUBING

BACKGROUND OF THE INVENTION

The invention relates to apparatus for pressure testing tubing.

Apparatus of this type is known from U.S. Pat. No. 1,637,956. This apparatus, however, is only useful for pressure testing rigid tubing because the ends of the tubing are supported and sealed by two spigots or support members urged together axially, the spigot forming a stationary tube support having an inlet duct for the test medium. This known apparatus is not suitable for testing flexible tubing, because it cannot seal the test medium into the test piece. Moreover, an actuating spindle in the known apparatus is the sole drive for the movable support member. If the metal-to-metal contact line between the conical end of the spigot and the tube is to be adequately sealed, extraordinarily high forces must be used to lead to a small plastic deformation of the edge of the tubing. If the seal is broken during the test, the test medium escapes at high pressure and there is a substantial risk to the person carrying out the test.

German Patent Specification No. 440,669 describes two different test devices which, like the above described apparatus, can only be used for rigid tubes. Moreover, they test the tubes only for their lengthwise strength and this necessarily precludes compressing the tubes by driving in a conical spigot. In one device, only tubes with flanges at each end can be tested, the sealing being effected at each end by a hydraulic piston. There is a rack and pinion, but this has no self-adjusting action and is not connected in tandem with the hydraulic drive serving only for the adjustment, off load, of one piston. In the other device, one of the hydraulic pistons is not required and it is retracted by the rack and pinion. In both cases, test medium is led into the tubing from the end remote from the mechanical adjustment device and this also excludes the testing of flexible tubes.

Test pressures are often greater than 1000 bar and thus the main problem is usually that of locating and sealing the test piece. There are many different variables to be accommodated—there are differences in nominal bore, types of connector, length of the test piece, forms of the two ends of the tube, and so on. Alone, the connector can have further variations, such as metric or imperial thread, external or internal thread, sloppy and tight tolerances in bore size, angled fittings with bends of 30°, 45°, 60°, 90°, and so on. The possible variations are further augmented by the option of screw fittings and press fittings. The two systems have different external dimensions. If you multiply all the variables, you get a theoretic number of $10^6$ types.

With such a multiplicity, the task of connecting a tube for a pressure test is extraordinarily costly, not only because you have to have a whole range of adapters for the two ends of the tube but also because of the time taken to set up the test.

For example, you might have to thread a complementary adapter to a metal connector before carrying out the test. This means, however, that you have to have a suitable adapter for each type of connector likely to be submitted for test.

It is also known to seal connectors by means of a ring that cuts into them with an encircling nut. This, however, is not possible for a large number of fittings, such as so-called tube-reinforcing fittings.

It is furthermore known, for pressure testing, to insert a spigot into the bore of the connector and seal it by means of washers. The wear on the washers is substantial, however, and moreover, the bore tolerances are usually so sloppy that the washers cannot fill the gaps. The washer is thus frequently pressed into the space between the spigot and the bore and the seal is broken at high pressure.

SUMMARY OF THE INVENTION

The main object of the invention is to solve the problem of making an apparatus of the type above described which is especially useful for flexible tubing, does not need an extensive number of adaptors and maintains a satisfactory seal even though it only needs low actuating forces in the mechanical part of the operating arrangement.

The problem is solved in apparatus of the above described kind, according to the invention, in that between the actuating spindle and the support member, a fluid pressure drive is arranged comprising a piston and cylinder which is connected in tandem with the actuating spindle and in that the movable spigot has a duct through which a test medium can be led into the tubing.

By virtue of the tandem arrangement of the actuating spindle and fluid pressure drive it becomes possible to use the actuating spindle substantially solely for bringing the support member with the conical spigot up to the tubing. This does not require any great actuating forces. The essential sealing for the test process is then effected by the fluid pressure drive which maintains a permanent seal by virtue of its inherent elasticity, even if elastic deformation in the mechanical system would otherwise cause the seal to be broken.

Associating the duct for leading in the test medium with the spigot on the driven support member is also essential for being able to pressurise flexible tubes, as the counter-bearing arrangement in which spigots are urged together as in U.S. Pat. No. 1,637,956 cannot be used at the opposite end of a flexible tube. Clearly, sealing must be done there in a different way.

The conical form of the spigot makes it suitable for a very large number of different bore diameters of tubingend-connectors. The spigot, whose conical face is suitably hardened, produces, when the support members are urged together, a small but smooth plastic deformation in the form of a chamfer where it meets the rim of the bore which makes for a dependable seal, but which is of absolutely no consequence as regards the further use of the tubing. The device is easy, quick and reliable even when used by untrained personnel, so that testing an entire production run does not involve any undue cost.

It is particularly useful to form the support member that carries the spigot as a housing and to mount the spigot removably therein by means of a coaxial cylindrical projection having two ring seals between which is located the inlet port for the test medium. In this manner, the axial force of the test medium on the insertable projection is neutralized so that the spigot is carried in the housing without the need for any additional securing arrangement. This has the additional advantage that even small connectors can be reliably engaged with the test apparatus, because the spigot acts as a piston and will load the armature so that it cannot compress and bend.

The angle of the cone can be varied within wide limits according to the intended use. Narrow cones can be inserted in very thick-walled connectors, while obtuse cones can be used with thin-walled connectors, whereby the forces tending to expand them are reduced to a harmless level.

So far as concerns the counter-bearing for metal connectors, it is particularly useful if it comprises clamp members movable radially to the metal connector and these are mounted on the supporting member for the counter-bearing. As the supporting member is generally formed from a rigid plate, the clamp members can be arranged to pivot parallel to the surface of the plate. As long as no other forces act on the connector, the clamps are easily pivotable radially to the connector. However, as soon as the pressure of the spigot and/or the test medium acts on the counter-bearing, the clamp members are pressed against the support member and are then held against lateral displacement.

It is hereby particularly advantageous to support the clamp members pivotally on the axes lying diametrically of the axis of the connector. In this manner, a sort of knee-joint system is formed in relation to the connector, which ensures a positive clamping of the connector.

It is also particularly advantageous to support the clamp members directly on the guide rails on which the housing for the spigot runs, as these are very stable elements of the assembly. In any event, this avoids the need to provide special pivot axes.

To make the apparatus useful for a plurality of different connectors, it is further of advantage to provide the clamp members with replaceable inserts adapted to the dimensions of the connectors. To adapt the apparatus, it is necessary to change only the inserts.

The shape of the insert is referred to hereinafter, however it is only necessary that the clamp members with their inserts grip the connector when closed in such a way that they securely take up the driving forces transmitted from the spigot to the connector. Furthermore, it is necessary that penetration of the actual flexible tubing is not prevented by the clamp members, as the tubing itself cannot withstand axial forces.

It is furthermore advantageous if the lengthwise axes of the counter-bearing, rails, spigot, piston and actuating spindle lie in a common plane. In this way, no harmful lateral forces or bending moments can arise.

Examples of an apparatus for pressure testing tubing according to the invention are hereinafter described with reference to the attached drawings wherein:

BRIEF DESCRIPTION OF THE DRAWINGS

FIGS. 1–3 are a side view, a part horizontal section and a front view respectively of the apparatus according to the invention and with the clamp members open, FIGS. 4–6 are side, part horizontal sectional and front views respectively of the apparatus of FIGS. 1 to 3 with a tube inserted and with the clamp members closed.

DETAILED DESCRIPTION OF THE PREFERRED EMBODIMENTS

Figure 7:
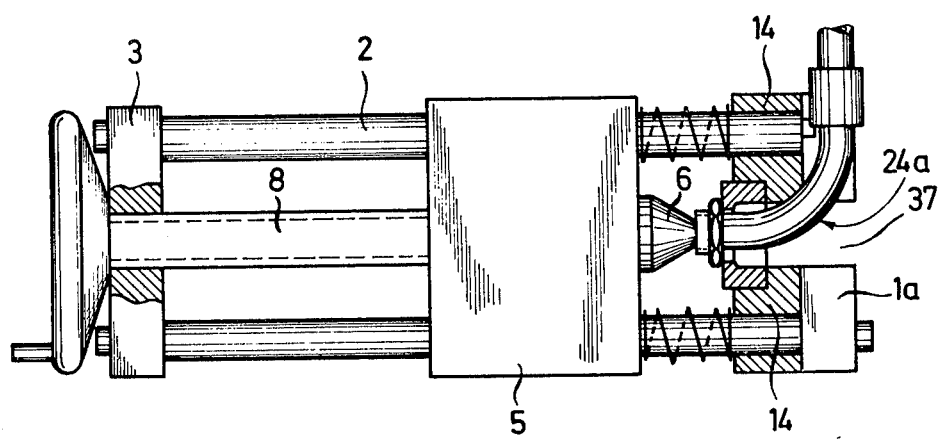
FIG. 7 is a part horizontal section of a variant of the apparatus shown in FIGS. 1 to 6 specially adapted for the pressure testing of flexible tube members with elbowed connectors.

In FIGS. 1–6, a support member 1 is shown which is connected by two parallel rails 2 with a yoke plate 3. The assembly is secured by screws 4. A support member 5 for a spigot 6 is guided on the rails so as to be slidable lengthwise by means of a drive 7. The drive 7 includes an actuating spindle 8 which is carried in a corresponding threaded part in the yoke plate 3 and adjusted rotationally by a hand wheel 9.

The support member 5 is formed as a housing. A cylinder 10 is formed in it in which a piston 11 is arranged so as to be slidable lengthwise of the rails. The cylinder 10 is connected by a pressure lead 12 to a source (not shown) of fluid pressure (hydraulic assembly). The pressure side of the piston is directed towards the spigot 6, while the actuating spindle 8 is carried in the side of the piston 11 remote from the pressure side. The effects of the actuating spindle 8 and piston 11 are additive or subtractive, that is to say, after pre-setting the support member 5 by means of the actuating spindle 8, the support member 5 can be moved further to the right in the direction of the support member 1 in relation to the piston 11 through the action of its pressure means.

On the rails 2 are arranged pressure springs 13 which at one end abut against the support member 5 and at the other end, through clamp members 14 to be referred to below, against the support member 1. By suitable pre-loading of the pressure springs 13, it is arranged that any possible play between the actuating spindle 8 and the yoke plate 3 is taken up and that the piston 11 is always forced to a position as far as possible within the support member 5.

The spigot 6 consists of hardened steel and has a conical face 15 of which the narrow end faces the support member 1, as well as a coaxial cylindrical projection 16 on which two spaced apart ring seals 17 and 18 are arranged lie in annular grooves. Between the seals 17 and 18 is a further annular groove 19. The projection 16 is carried in a corresponding cylindrical base 21 of the support member 5 into which, at the position of the groove 19, a pressure duct 20 opens. The duct is connected to a source of pressure test medium. Into the groove 19, there also opens a duct 22 coaxial in the spigot 6, the other end of which opens at the tip of the conical surface 15. The construction of the projection 16 and the cylindrical bore 21 is such that the spigot 6 is removably carried in the support member 5. When pressure is applied through the pressure inlet 20 the axial forces are neutralized so that the spigot 6 is not forced out of the cylindrical bore 21.

On the support member 1 is a counter-bearing 23 for a metal connector 24 to be further described below. The counter-bearing 23 comprises two clamp members 14, movable radially with respect to the metal connector 24 (FIGS. 3 and 6), which can abut against the support member 1, under the action of forces from the pressure springs 13 as well as from the metal connector. The clamp members 14 are mirror-symmetric and pivoted on two axes 25 and 26 lying diametrally with respect to the axis of the connector. The relationship to the connector axis is clear with reference to the locked position shown in FIG. 6. In this way, there is formed a toggle joint system which holds fast when high loading forces are applied to the metal connector in the pressure-on position shown in FIG. 6. The axes 25 and 26 are in this embodiment coaxial with the lengthwise axes of the rails 2, that is to say, the clamp members 14 are carried directly on the ends of the rails 2 adjacent the support member 1.

In the clamp members 14, bolt-like studs 27 and 28 are inserted which (in the closed position of the clamp members seen in FIG. 6) lie to one side of the line connecting the pivot axes 25 and 26. At least one of the studs 27 and 28 is adjustable parallel to the said connecting line. It is seen from FIG. 6 that a different terminal position of the clamp members can be set by adjusting one of the studs 27, 28. This terminal position should be so adjusted in this way that the end of the metal connector 24 that cooperates with the spigot 6 is exactly aligned with the axis of the spigot.

In the clamp members are fixed inserts 29 and 30 adjusted to the dimensions of the metal connector 24 which are formed as annular sectors. The inserts have parts 31 of increased internal diameter whereby to ensure that when tightening the clamp members on the rubber covering of a flexible tube behind the connector, the flexible material is more lightly compressed so that the tightening force is reduced. The inserts 29 are each held in the clamp members 14 by a radially fixed bolt 32 and a radially movable bolt 33. The movable bolts 33 are provided with knobs 34 and are preferably spring loaded inwards. After pulling out the bolts 33 the inserts can easily be removed from the fixed bolts 32. By the relative radial positions of the fixed and movable bolts, the inserts are securely locked in position.

It is seen from FIGS. 1 to 3 that the lengthwise axes of the counter-bearing 23, rails 2, spigot 6, piston 11 and actuating spindle 8 lie in a common plane which coincides with the plane in which is taken the section of FIG. 2. In this manner, no lateral forces can arise which would cause undesired flexure of the constructional elements. The whole apparatus is carried by profiled bolts 34 so as to be displaceable in the direction of the rails 2 in guide members 35, which are shown only by broken lines in FIG. 1.

The way in which the above described apparatus is used will be understood from a comparison of FIGS. 1 to 3 with FIGS. 4 to 6. In FIGS. 1 to 6 like reference numerals are used for like parts.

First, the end of the metal connector 24 in FIG. 3 is fed between the inserts 29 and 30 of the already opened clamp members 14. The connector 24 comprises, as seen in FIG. 5, a hollow connecting pipe 24a on which a flexible tube 24b is push-fitted. Of this tubing 24b, which is crimped onto the connector 24a by means of a sleeve 24c, only the outer shell—the rubber covering—is visible. This covering is brought into position by being inserted radially into the inserts 29 and 30 while the sleeve 24c is brought into position in the axial direction into the inserts 29 and 30. If now one or the other clamp member 14, for example by means of the lever 36, is pivoted from the position shown in FIG. 3 to the pressure-on position shown in FIG. 6, the other clamp member 14 is carried with it symmetrically and synchronously. The flexible tubing is then securely clamped as shown in FIGS. 4 to 6.

By turning the actuating spindle 8 the support member 5 is pushed forward to bring the spigot 6 against the metal connector 24 until the spigot enters the connector bore and lies against the annular rim. Then the cylinder 10 is charged with pressure fluid through the inlet 12, whereby the conical face 15 of the spigot 6 is pressed against the annular rim of the connector. This produces a small plastic deformation of this rim which forms a smooth, sealing face against the conical face 15. The opposite end of the flexible tube 24b is closed in similar fashion.

Then a test medium is fed to the tubing and the metal connector through the pressure inlet 20 (FIG. 2) which fills the test sample and pressurizes the gas therein. After completely ventilating the system, the test sample is subjected to the above described test pressure of, for example, 1000 or 1500 bar. The subsequent relief of the pressure can be carried out in a simple manner, namely by gradually taking off the loading of the cylinder 10 and piston 11. In order to extract the test sample from the apparatus, the support member 5 with the spigot 6 is moved back to the left by the actuating spindle 8, whereupon the test cycle can be repeated on another test sample.

FIG. 7 shows a modified apparatus like that in FIGS. 1 to 6, which is particularly suitable for metal elbow connectors 24a. For this purpose, the support member 1a is provided with a U-shaped recess 37 open in the direction of the opening of the clamp members 14. The rest of the components of the apparatus are the same.

It is important in regard to the object of the invention that the thread of the actuating spindle 8 has such a fine pitch that it is substantially self-locking, that is to say it will not automatically run back under the influence of the pressure drive. In this event the tandem connection of the spindle drive and pressure drive would be substantially useless. Self locking of the spindle could also be brought about even with a coarser pitch if the spindle were provided with a braking arrangement.

What is claimed is:
1. Apparatus capable of use in pressure testing flexible tubing ending with a metal connector, comprising:
a first and a second support member;
means mounting the first support member for movement towards and away from the second support member;
a spigot on the first member and having a conical face for coaxial insertion into the end of the metal connector when the first support member is moved toward the second support member;
mechanical means for so moving the first support member;
pressure drive means disposed in the first support member and connected between the spigot and the mechanical means for moving the spigot away from the mechanical means and into sealing engagement with the end of the metal connector;
a duct through the spigot for introducing pressure-testing fluid into the flexible tubing; and
holding means on the second support member for holding the metal connector with the end thereof facing the spigot, the holding means comprising two clamp members each pivotally mounted on the second support member for closing movement about the metal connector.

2. The apparatus according to claim 1, wherein the pivot axes of the clamp members lie on a diameter of the connector when held therein.

3. The apparatus according to claim 1, wherein the clamp members have complementary, removable inserts corresponding to the dimensions of the connector.

4. The apparatus according to claim 1, wherein the pressure drive means comprises: a cylinder in the first support member opposite the spigot; a piston in the cylinder and connected to the mechanical means; and means for communicating a pressurized fluid through the first support member and into the cylinder.

5. The apparatus according to claim 4, wherein the first support member has a bore therein facing the second support member and means for providing the pressure-testing fluid to the bore, and the spigot has means for removably mounting the same in the bore comprising a coaxial cylindrical projection and two ring seals between which is a radial entry port for the duct for the pressure-testing fluid.

6. The apparatus according to claim 4, wherein the means mounting the first support member for movement comprises a yoke plate, parallel rails connected at one end to the yoke plate and at the other end to the second support member, and means mounting the first support member for sliding lengthwise of the rails; and wherein the mechanical means comprises an actuating spindle carried in the yoke plate.

7. The apparatus according to claim 6, wherein the pressure side of the piston is directed towards the spigot and the other side of the piston is connected to the actuating spindle.

8. The apparatus according to claim 6, wherein the clamp members are pivoted on the rails.

9. The apparatus according to claim 6, wherein the means mounting the first support member further comprises pre-loaded pressure springs on the rails which at one end abut against the clamp members and at the other end, against the first support member.

10. The apparatus according to claim 6, wherein the pivot axes of the two clamp members, and the axes of the rails, spigot, piston and actuating spindle lie in a common plane.

* * * * *